United States Patent [19]

Cabi-Akman et al.

[11] Patent Number: 4,569,594
[45] Date of Patent: Feb. 11, 1986

[54] COLOR VALUE MEASUREMENT

[75] Inventors: Robert Cabi-Akman, Echandens; Rémy Simond, La Tour-de-Peilz; Arthur Sprenger, Saint-Légier, all of Switzerland

[73] Assignee: Nestec S.A., Vevey, Switzerland

[21] Appl. No.: 532,073

[22] Filed: Sep. 14, 1983

[30] Foreign Application Priority Data

Oct. 14, 1982 [CH] Switzerland .................. 5995/82

[51] Int. Cl.[4] .................... G01J 3/51; G01N 21/27
[52] U.S. Cl. ................................ 356/408; 356/243
[58] Field of Search ............... 356/243, 406, 408, 418, 356/421, 422, 423, 424, 425, 30; 250/233

[56] References Cited

U.S. PATENT DOCUMENTS

| | | | |
|---|---|---|---|
| 2,339,976 | 1/1944 | Brown | 250/233 |
| 3,363,108 | 1/1968 | Spurr et al. | 356/421 |
| 3,467,475 | 9/1969 | Celio et al. | 356/408 |
| 3,500,050 | 3/1970 | Hillman | 250/233 |
| 3,623,817 | 11/1971 | Celio | 356/408 |
| 3,735,143 | 5/1973 | Langford | 356/408 |
| 3,794,424 | 2/1974 | Eickhorst et al. | 356/425 |
| 3,874,799 | 4/1975 | Isaacs et al. | 356/236 |
| 4,029,419 | 6/1977 | Schumann, Jr. et al. | 356/418 |
| 4,131,367 | 12/1978 | French et al. | 356/425 |
| 4,176,963 | 12/1979 | Fabinski et al. | 356/408 |
| 4,319,847 | 3/1982 | Howarth | 356/243 |
| 4,464,054 | 8/1984 | Karras et al. | 356/416 |

Primary Examiner—F. L. Evans
Assistant Examiner—Joel L. Harringa
Attorney, Agent, or Firm—Vogt and O'Donnell

[57] ABSTRACT

Figure 1:
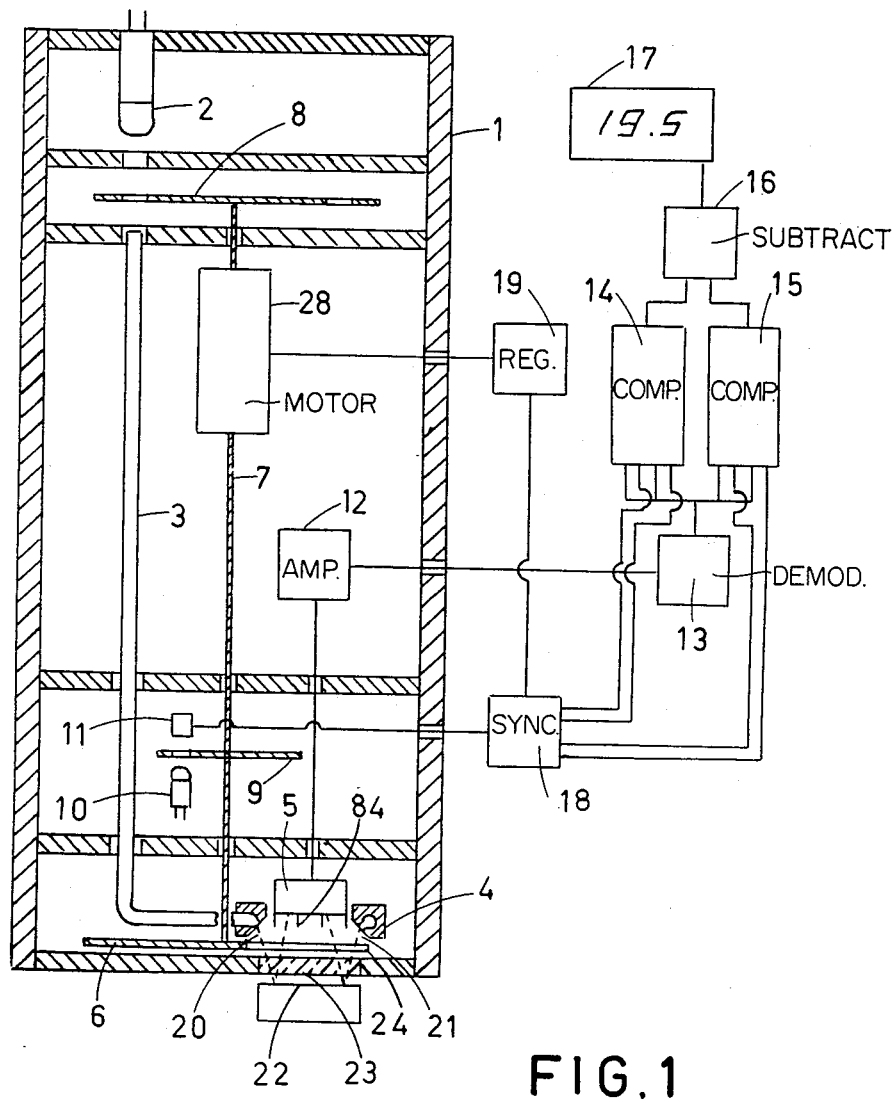

A sample to be measured, a black reference and at least one reference having a color similar to that of the sample are exposed successively and cyclically to the same incident light beam, the light beams which are reflected successively by the sample and the references are detected photoelectrically, the ratio of the intensities of the light beams reflected by a sample and one reference color on the one hand and by the black reference and a reference color on the other hand is established electronically, the second ratio is subtracted electronically from the first and a difference which is directly proportional to the brilliance of the color of the sample is automatically obtained during each exposure or measurement cycle at a determined measurement frequency (FIG. 1).

10 Claims, 5 Drawing Figures

COLOR VALUE MEASUREMENT

This invention relates to a process for measuring the brilliance of a colour by comparison.

The present invention also relates to an apparatus for measuring the brilliance of a colour by comparison, comprising a light source, an optical device to form and direct an incident light beam onto a sample to be measured and onto a colour reference, a photodetector to produce electrical signals in response to the detection of light beams which are reflected by the sample and the reference, and an electronic circuit to process and compare said electrical signals.

Various processes and apparatus for measuring colour are known which are based on the principle of comparison, for example between a colour reference and a sample to be measured. Some are intended for a true colour measurement by analysing the components of the colour according to an internationally accepted system, such as the Munsell system in which a colour is defined by its shade, its brilliance and its saturation. Others are intended for the regulation of industrial installations or apparatus as a function of the colour of the products which are obtained, or they are intended for sorting of, for example products having a variable colour. In these cases, a true or complete measurement of the colour is often not adequate, and processes and apparatus based on the measurement of a single component of the colour, for example its brilliance or its shade, are known.

However, quite generally, whether it is a question of a measurement of the complete colour or of only one of its components, it is found that the handling of known apparatus, even the most perfected and the most modern apparatus could be made even easier.

In a recent known colorimeter, before making a colour movement by comparison, a known colour reference has to be introduced into the apparatus, the apparatus has to carry out an analysis of the reference and memorise it, and then the sample of an "unknown" colour has to be introduced in order to obtain a determination of its colour.

In another type of known colorimeter, comprising a light source, an optical device for producing two light beams from this source, and two phototubes for detecting the two beams which are reflected by a sample on the one hand and by a colour reference on the other hand, the operator himself must constantly maintain the balancing of the circuit connecting the two phototubes so that the comparison of the two measurements is valid.

For certain routing measurements concerning colours which are always similar, or for example for certain regulation or sorting processes, it would be useful to have a process and an apparatus which allow a measurement by comparison to be made practically permanently, without the operator having to press any adjustment or balancing button and without standardisations having to be carried out too frequently.

An object of the present invention is to provide a simple process and apparatus which are suitable for measuring the brilliance only of a colour and are based on the principle of an automatic and practically permanent comparison.

To this end, the process according to the present invention is characterised in that a sample to be measured, a black reference and at least one reference colour similar to that of the sample are successively and cyclicly exposed to the same incident beam of light, the light beams which are successively reflected by the sample and the references are detected photoelectrically, the ratio of the intensities of the light beams reflected by the sample and a reference colour on the one hand and by the black reference and a reference colour on the other hand is established electronically, the second ratio is subtracted electronically from the first and a difference which is directly proportional to the brilliance of the colour of the sample is automatically obtained in each exposure or measurement cycle, at a determined measurement frequency.

Likewise, the apparatus according to the present invention is characterised in that it comprises a black reference and at least one reference colour similar to that of the sample, an exposure device for exposing the sample, the black reference and the colour reference successively and cyclicly to an incident light beam, two electronic comparison circuits for establishing the ratios of the intensities of the light beams reflected by the sample and a reference colour on the one hand and by the black reference and a reference colour on the other hand, and an electronic subtraction circuit for establishing in each exposure or measurement cycle a difference between these two ratios which is directly proportional to the brilliance of the colour of the sample.

The notion of the brilliance of a colour is used in the present description in the sense ascribed thereto by the "Munsell" system which has been mentioned above. The brilliance corresponds to the light intensity of a colour, as opposed to its shade characterised by a dominant wavelength, as well as opposed to its saturation or purity. The brilliance is the equivalent of the Y component, obtained through a green filter in the CIE system (Commission Internationale de l'Eclairage) [International Lighting Commission] in which the trichromatic components X, Y and Z of a colour are defined by the amount of light passing through red, green and blue filters.

Thus, the present process and apparatus make it possible to determine cyclicly, at a determined measurement frequency, a magnitude which is directly proportional to the brilliance of the colour of the sample. In fact, by establishing the ratio of the intensities of the light beams reflected by the sample and one reference colour, all the proportional variations of these intensities are eliminated, in particular those which are due to the overheating and ageing of certain elements, such as the light source and photodetector or certain electronic circuits which are used for carrying out the process or are used in the construction of the apparatus. Moreover, by establishing the difference between this first ratio and the ratio of the intensities of the beams reflected by the black reference and one reference colour, the effect of parasitic rays of light which are reflected by something other than the sample or the references is eliminated.

If the colour brilliance is plotted graphically as ordinate and the magnitude determined by the present process is plotted as the abscissa, an ascending straight line is produced, the slope of which may be modified by multiplying electronically the first ratio by a first constant, and the origin of which may be moved by multiplying electronically the second ratio by a second constant. Once the slope and the origin of the stright line have been fixed, this origin does not move any more during the measurements, any deviation which is due to the above mentioned reasons being automatically compensated and eliminated in each cycle. Thus, it is possible to say that a calibration and a setting to zero are thus automatically produced in each measurement cycle from a comparison with a black reference and with at least one colour reference.

Two references of a similar colour are preferably used, the known brilliances of which are respectively high and medium, and the ratio of the intensities of the light beams reflected by the sample and the colour reference of a high brilliance on the one hand and by the black reference and the colour reference of a medium brilliance on the other hand is established. In this manner, it is even possible to exercise an improved control over the direct proportionality between the magnitude determined by the present process and the brilliance of the colour of the sample. In fact, each of the parameters concerned is thus acted on more specifically and with a greater degree of precision, in that the control of the slope of the straight line mentioned above will be more precise if it is effected with respect to a colour reference of a high brilliance (located at the top of the straight line), whereas the control of the origin of this straight line will be more precise if it is effected with respect to a colour reference of a medium brilliance (located at the bottom of the straight line).

In a preferred embodiment of the process and the apparatus, the incident light beam is chopped at a determined chopping frequency and, after the photoelectronic detection, those electrical signals, the frequency of which differs from the chopping frequency, are eliminated. This precaution is intended in particular for the elimination of parasitic signals of an external origin, such as natural ambient light (component of a constant intensity) or artificial ambient light (component of an intensity which oscillates at a frequency double that of the network).

The apparatus according to the present invention will now be described in more detail in the following with reference to the accompanying drawings which are provided by way of example.

Figure 2:
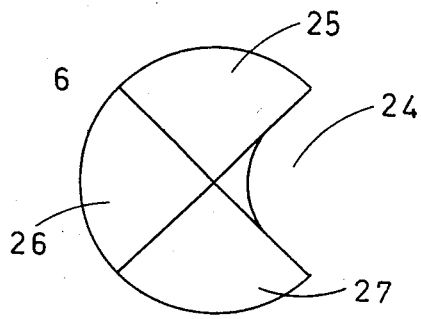
Figure 3:
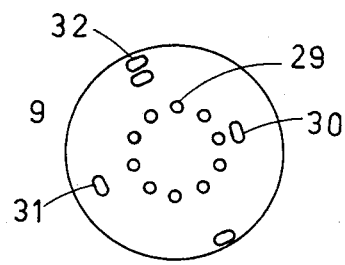
Figure 4:
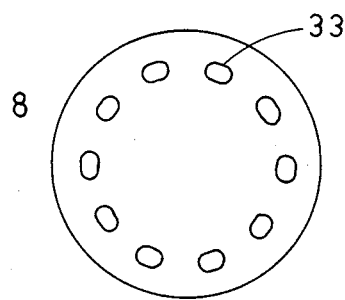
Figure 5:
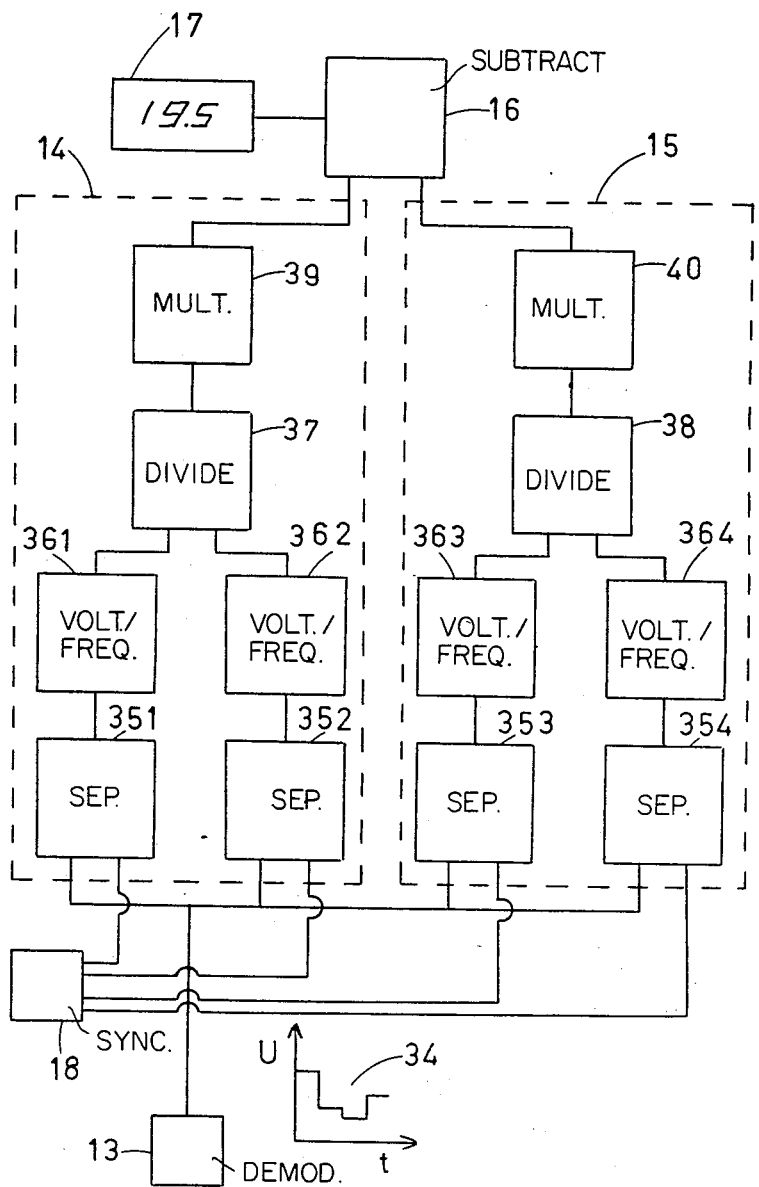

FIG. 1 is a diagram of one embodiment of the present apparatus in which the optical and mechanical devices are shown in section, FIG. 2 shows an exposure disc, FIG. 3 shows a synchronisation disc, FIG. 4 shows a chopper disc, and FIG. 5 is a block diagram of the electronic comparison and subtraction circuits.

The apparatus which is shown schematically in FIG. 1 comprises, in a light-tight box 1, a light source 2, an optical device 3, 4, a photodetector 5 and an exposure device 6. In the embodiment which is shown in this figure, the box 1 also comprises a light chopping device 8 and a sychronisation device 9, 10, 11.

The electronic part comprises an amplification circuit 12 in the box 1, and outside the box, a demodulation circuit 13, two comparison circuits 14, 15, a subtraction circuit 16, a digital display device 17, a synchronisation circuit 18 and a regulation circuit 19.

The apparatus functions as follows. The light from the source 2, for example a halogen lamp is guided by optical fibres 3 to an annular distributor 4 which forms a conical incident light beam or a beam having several converging rays 20, 21, that is, some rays defining a few positions of the directrix of the same cone. The beams reflected by the surface to be measured 22 (and 15–27 FIG. 2) are detected by the photodetector 5, for example a silicon photovoltaic cell, positioned in the center of the distributor 4. A grid 84 is provided in front of the photodetector 5 to intercept the light rays which do not come from the surface to be measured.

In the embodiment shown in FIG. 2, the exposure device is produced in the form of a rotary disc 6 divided into an open sector 24, a black reference sector 25 and two reflecting sectors of a similar colour, the brilliances of which are resepectively medium 26 and high 27. This rotary disc 6 is fixed to the end of an axle 7 driven by the motor 28 (M) at a rotational speed which, expressed in revolutions/s (Hertz) represents the measurement frequency. When the open sector 24 passes over a window 23, the light beam is reflected by the sample 22. The beam is then reflected by the black reference 25 and by the colour references 26, 27 when the sectors bearing these references pass successively between the window 23 and the photodetector 5. The measurement frequency may be, for example about 1 Hertz. It is regulated by the synchornisation device.

In the embodiment shown in FIG. 3, the synchronisation device is produced in the form of a synchronisation disc 9 which is pierced by holes 29–32. This rotary disc 9 is also fixed to the axle 7 driven by the motor 28. The holes of the disc 9 are intended to pass at the said measurement frequency between at least one auxiliary light source 10 and at least one auxiliary photodetector 11 to produce electrical synchronisation signals. In the embodiment shown in FIG. 3, the holes are positioned over four concentric circles. One auxiliary light source auxiliary photodetector pair, for example a transmitting diode-phototransistor pair, corresponds to each circle.

The signals which are emitted correspond to the holes 29 located on the center-most circle of the disc are for the regulation of the driving means 7, 28 of the exposure device 6. These signals are processed by the synchronisation circuit 18, and then by the regulation circuit 19 which controls the motor 28.

The signals which are emitted corresponding to the holes 30, 31, 32, located on the following circles are for the synchronisation of the electronic comparison circuits 14 and 15 by means of the synchronisation circuit 18.

FIG. 4 shows an embodiment of the light chopping device, that is, a rotary chopper disc 8 which is pierced by numerous openings 33 arranged in a circle. This disc is also driven by the motor 28, but at several times the rotational speed of the axle 7 in order to alternately cut off and let through the light from the light source 2 at a relatively high chopping frequency. If a chopping frequency of, for example 200 Hertz is desired, and if the disc has ten openings, as in FIG. 4, the chopper disc will be rotated twenty times faster than the measurement disc if the latter is regulated at a frequency of, for example 1 Hertz.

The amplification circuit 12 and the demodulation circuit 13 successively process the electrical signals delivered by the photodetector 5. The amplification circuit 12 is preferably positioned in the box 1 of the apparatus in order to avoid any parasitic disturbance of the very low intensity signals from the photodetector 5 during their transport to an external box containing the various electronic circuits. The function of the demodulation circuit 13 is to re-establish constant voltage levels corresponding to the intensity of the reflected light beams from pulses which arrive there at the chopping frequency. Any signal, the frequency of which differs from the chopping frequency is eliminated at the stage of these two circuits of amplification 12 and of demodulation 13.

The design and the operation of the comparison and subtraction circuits 14, 15 and 16 will now be described in the following with reference to FIG. 5 which shows a block diagram of the comparison circuits. The demodulated periodic signals originating from the demodulation circuit 13 have the shape which is indicated by reference numeral 34, that is, four separate voltage levels corresponding to the intensities of the light beam reflected by the sample and the references. Each of these levels is separated and maintained constant for the duration of a complete revolution of the exposure disc 6 in four separator circuits 351–354 synchronised with the signals originating from the synchronisation disc 9 marking the passage of the sectors of the exposure disc 6, signals which are processed and transmitted to said separator circuits by the synchronisation circuit 18.

There are four separate voltages at the output of the four separator circuits, which voltages are converted into four separate frequencies in four converter circuits 361–364 to increase the precision and the stability of the subsequent operations. The comparison is then made, i.e., the ratio of these frequencies is established in pairs in two divider circuits 37 and 38 which are both designed on the principle of counting one frequency in a counter (not shown) and deducting the other frequency in a second counter (not shown) to the rhythm of a reference frequency provided by a clock (not shown).

The two relatively reduced frequencies resulting from establishing the two ratios in the divider circuits 37 and 38 are then each multiplied by the same factor in two multiplier circuits 39 and 40 in order to find a higher frequency level.

The two frequencies delivered by the circuits 39 and 40 are proportional to the ratios of the intensities of the light beams reflected by the sample and the colour reference of a high brilliance on the one hand and by the black reference and the colour reference of a medium brilliance on the other hand. The second of these frequencies is then substracted from the first in the subtraction circuit 16 which is designed on the principle of counting one frequency and deducting the other frequency in the same counter (not shown) to the rhythm of another reference frequency provided by a clock (not shown).

The difference which is thus obtained to the rhythm of the measurement frequency is directly proportional to the brilliance of the colour of the sample. it is transmitted to a decoder circuit included in the display device 17 which allows the permanent display of a value which is determined during each measurement cycle and is directly proportional to the brilliance of the colour of the sample.

We claim:

1. A process for measuring the brilliance of a colour sample, which comprises:
   (a) exposing the sample, a black reference and one or more reference samples having a colour similar to the colour sample, cyclicly at a determined frequency to the same incident light beam;
   (b) detecting photoelectrically the intensity of the light reflected by said colour sample and references;
   (c) calculating electronically a first ratio of the intensity of the light reflected by said colour sample to the intensity of the light reflected by one of said reference samples, and a second ratio of the intensity of the light reflected by said black reference to the intensity of the light reflected by one of said reference samples; and
   (d) subtracting electronically the second ratio from the first ratio
to thereby obtain a value which is directly proportional to the brilliance of the colour sample.

2. A process as claimed in claim 1, wherein two reference samples are used, one having high brilliance and the other having medium brilliance, and the ratio of the intensitities of the light reflected by the colour sample and the reference sample of high brilliance on the one hand, and by the black reference and the reference sample of medium brilliance on the other hand is established.

3. A process as claimed in claim 1, further comprising chopping the incident light beam at a determined chopping frequency and, after the detection step, eliminating electrical signals the frequency of which differs from the chopping frequency.

4. An apparatus for measuring the brilliance of a color sample, which comprises:
   (a) a light source;
   (b) means for exposing cyclicly at a measurement frequency a colour sample, a black reference and one or more reference samples having a colour similar to the colour sample to an incident light beam;
   (c) means for detecting light reflected from the sample and references, said detecting means producing electrical signals in response to the intensity of said reflected light;
   (d) means for processing the electrical signals from said detecting means, and establishing the ratio of the intensities of the light reflected by the colour sample and one of said reference samples, and the ratio of the intensities of the light beams reflected by the black reference and one of said reference samples; and
   (e) means connected to said processing means for establishing the difference between said ratios;
said difference being directly proportional to the brilliance of the colour sample.

5. An apparatus as claimed in claim 4, wherein the exposing means comprises a rotary exposure disc rotatably mounted in the path of the incident light beam, and means for rotating said disc, said disc containing said black reference incorporated into a black reference sector, said reference samples incorporated into two reference sectors of similar colour of respectively medium and high brilliance, the incident light beam being directed onto the exposure disc between its edge and its center so that the beam successively sweeps over each of the said sectors, and the processing means estalishes the ratio of the intensities of the light beams reflected by the colour sample and by the reference sector having a colour of high brilliance, and the ratio of the intensities of the light beams reflected by the black reference sector and the reference sector having a colour of medium brilliance.

6. An apparatus as claimed in claim 4, which also comprises at least one auxiliary light source, at least one auxiliary photodetector, and a rotary synchronisation disc pierced by holes rotatably mounted between one of said auxiliary light sources and one of said auxiliary photodetectors to produce electrical synchronisation signals, said holes allowing light from said auxiliary light source to contact said auxiliary photodetector at said measurement frequency, means for rotating said synchronisation disc, and an electronic synchronisation circuit to regulate said rotating means for the said exposing means, and to synchronise the said processing means.

7. An apparatus as claimed in claim 4, which also comprises a light chopping device which is in the form of a rotary chopper disc pierced by numerous openings, said disc being rotatably mounted between said light source and said exposing means, said openings upon rotation of said disc being operative to alternately cut off and let through light from the light source at a determined chopping frequency, and further comprises means for rotating said chopper disc, and electronic circuits for amplifying and demodulating the electrical signals delivered by the detecting means.

8. An apparatus as claimed in claim 4, which also comprises a display device connected to said establishing means for the display of the value which is determined during each measurement cycle.

9. An apparatus as claimed in claim 4 wherein the detecting means includes a single photodetector.

10. An apparatus as claimed in claim 9, wherein the exposing means includes optical fibres and an annular distributor, the optical fibres guiding the light from the light source to said distributor which forms a conical incident light beam or a beam having several converging rays, and the photodetector being positioned in the center of the distributor.

* * * * *

UNITED STATES PATENT AND TRADEMARK OFFICE
CERTIFICATE OF CORRECTION

PATENT NO.   : 4,569,594
DATED        : February 11, 1986
INVENTOR(S)  : Robert Cabi-Akman, et al.

It is certified that error appears in the above—identified patent and that said Letters Patent is hereby corrected as shown below:

Column 1, line 38 "movement" should read -- measurement--.

Column 1, line 53 "routing" should read -- routine --.

Column 2, line 66 "stright" should read -- straight --.

Column 3, lines 67-68 "(and 15-27 Fig. 2) "should read -- (and 25-27 Figure 2) --.

Column 5, line 49 "it" should read -- It --.

Column 6, Claim 5, line 54 "estalishes" should read -- establishes --.

Signed and Sealed this

Twenty-seventh Day of May 1986

[SEAL]

Attest:

DONALD J. QUIGG

Attesting Officer    Commissioner of Patents and Trademarks